US009713682B2

(12) United States Patent
Eistetter et al.

(10) Patent No.: US 9,713,682 B2
(45) Date of Patent: *Jul. 25, 2017

(54) DEVICE FOR DOSING AND DRY NEBULIZATION

(75) Inventors: Klaus Eistetter, Constance (DE); Wilhelm Wurst, Constance (DE); Gerhard Pohlmann, Meerbeck (DE); Horst Windt, Burgwedel (DE); Oliver Nolte, Celle (DE); Wolfgang Koch, Steimbke (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 1467 days.

This patent is subject to a terminal disclaimer.

(21) Appl. No.: 11/887,513

(22) PCT Filed: Apr. 7, 2006

(86) PCT No.: PCT/EP2006/003172
§ 371 (c)(1),
(2), (4) Date: Jan. 23, 2009

(87) PCT Pub. No.: WO2006/105980
PCT Pub. Date: Oct. 12, 2006

(65) Prior Publication Data
US 2009/0211577 A1   Aug. 27, 2009

(30) Foreign Application Priority Data
Apr. 8, 2005 (DE) .................. 10 2005 016 102

(51) Int. Cl.
*A61M 15/00* (2006.01)
*B05B 7/14* (2006.01)
(Continued)

(52) U.S. Cl.
CPC ........ *A61M 11/06* (2013.01); *A61M 15/0065* (2013.01); *A61M 15/0086* (2013.01);
(Continued)

(58) Field of Classification Search
CPC .. A61M 11/00; A61M 11/001; A61M 11/006; A61M 11/007; A61M 11/02;
(Continued)

(56) References Cited

U.S. PATENT DOCUMENTS 1,934,793 A * 11/1933 Crain et al. ..................... 604/58
1,988,017 A *  1/1935 Norwick ....................... 239/417
(Continued)

FOREIGN PATENT DOCUMENTS

FR          999959    * 10/1946
FR        2 257 351      8/1975
(Continued)

*Primary Examiner* — Kathryn E Ditmer
(74) *Attorney, Agent, or Firm* — Nath, Goldberg & Meyer; Jerald L. Meyer; Christopher Thomas

(57) ABSTRACT

The invention relates to a device 1 for dosing and dry nebulization of nebulizable material 12 chosen from the group comprising anti-infective agents and immunomodulators, comprising a nebulization channel 3, which has a first attachment piece and a second attachment piece, and a source of compressed carrier gas connected to the first attachment piece via a valve 16 for the purpose of sending a carrier gas pressure pulse into the nebulization channel. The device is characterized in that between the first attachment piece and second attachment piece, and above the nebulization channel, a reservoir 10 open only towards the nebulization channel, which contains the nebulizable material 12, is connected to the nebulization channel such that it is gas-tight with respect to the environment, and that, when the valve is closed, a pressure compensation takes place in the nebulization channel and in the reservoir. The invention (Continued)

also relates to a method for dosing and dry nebulization of such a nebulizable material by means of such a device.

15 Claims, 5 Drawing Sheets

(51) Int. Cl.
*A61M 11/06* (2006.01)
*A61M 16/14* (2006.01)
*A61M 16/20* (2006.01)
*A61M 16/00* (2006.01)

(52) U.S. Cl.
CPC .......... *A61M 16/14* (2013.01); *A61M 16/202* (2014.02); *B05B 7/1404* (2013.01); *A61M 11/065* (2014.02); *A61M 2016/0027* (2013.01); *A61M 2202/064* (2013.01)

(58) Field of Classification Search
CPC ......... A61M 11/06; A61M 13/00; B05B 7/14; B05B 7/1409
USPC ............ 128/200.14, 200.21, 200.22, 203.12, 128/203.15, 203.19; 222/630, 637; 239/143, 337, 338, 340, 345, 346, 376, 239/377, 379, 654
See application file for complete search history.

(56) References Cited

U.S. PATENT DOCUMENTS

| 2,570,774 | A | * | 10/1951 | Davis ....................... 128/203.15 |
| 3,442,454 | A |   | 5/1969  | Stenger et al. |
| 3,888,252 | A | * | 6/1975  | Side et al. ................ 128/203.15 |
| 4,071,170 | A | * | 1/1978  | Gunzel, Jr. .......... A01M 9/0046 222/199 |
| 4,502,640 | A | * | 3/1985  | Nonis ........................... 239/346 |
| 5,039,017 | A | * | 8/1991  | Howe ........................... 239/346 |
| 5,337,740 | A | * | 8/1994  | Armstrong et al. ...... 128/203.12 |
| 5,775,320 | A | * | 7/1998  | Patton ............... A61M 15/0065 128/200.14 |
| 5,875,776 | A | * | 3/1999  | Vaghefi .................... 128/203.15 |
| 6,014,972 | A | * | 1/2000  | Sladek ..................... 128/203.12 |
| 6,234,169 | B1 | * | 5/2001 | Bulbrook et al. ........ 128/203.15 |
| 6,681,767 | B1 |   | 1/2004 | Patton et al. |
| 2002/0158090 | A1 |   | 10/2002 | Odessa |
| 2003/0196660 | A1 | * | 10/2003 | Haveri ..................... 128/203.12 |
| 2004/0211419 | A1 | * | 10/2004 | Eason et al. ............. 128/203.15 |
| 2005/0121025 | A1 | * | 6/2005  | Gamard et al. .......... 128/200.23 |
| 2005/0183724 | A1 | * | 8/2005  | Gumaste et al. ........ 128/203.15 |

FOREIGN PATENT DOCUMENTS

| FR | 2 598 918 A1 |   | 11/1987 |
| FR | 2598918 A1 | * | 11/1987 |
| GB | 24848 |   | 0/1914 |
| GB | 2 310 816 A |   | 9/1997 |
| WO | WO 9007351 A1 | * | 7/1990 |
| WO | 92/10229 A1 |   | 6/1992 |

* cited by examiner

DEVICE FOR DOSING AND DRY NEBULIZATION

This is a National Phase Application filed under 35 U.S.C. §371 as a national stage of PCT/EP2006/003172, filed on Apr. 7, 2006, an application claiming the benefit under 35 U.S.C. §119 of German Application No. 10 2005 016 102.2, filed on Apr. 8, 2005, the content of each of which is hereby incorporated by reference in their entirety.

FIELD OF THE INVENTION

The invention relates to a device and a method for dosing and dry nebulization of nebulizable material, chosen in particular from the group comprising anti-infective agents and immunomodulators.

BACKGROUND OF THE INVENTION

Devices for dry nebulization of nebulizable material are known to the skilled person. In these devices, a nebulizable material, for example a powdered pharmaceutical preparation, is acted upon by a compressed gas or carrier gas in a specially provided chamber and, within this chamber, is converted to a state which is referred to as dry mist. The grains of the material are in this case present in a preferably uniform and finely dispersed form across the entire volume of compressed gas or carrier gas and are then discharged from the chamber in this state via suitable devices.

Such devices are used in particular to form pharmaceutical preparations for inhaled administration to spontaneously ventilating or ventilated patients. For use in spontaneously ventilating patients, the devices are generally connected to a suitable mouthpiece or a breathing mask. In invasive use, i.e. on ventilated patients, these devices are built into the respirator.

In the devices known hitherto for dry nebulization of nebulizable material, however, the problem generally found was that large amounts of pharmaceutical preparations could be delivered to the patient only, if at all, with considerable outlay in terms of equipment, for example using extensive mechanical dosing devices. Generally, the known devices were suitable for the nebulization of pharmaceutical quantities in the range from approximately 1 µg to approximately 20 mg. A simple system for dry nebulization of large amounts, in particular of powdered pharmaceutical preparations, for example of some 100 mg to 3 g, on patients has not hitherto been available.

In conventional dry nebulizers, a problem frequently found was that the nebulizable material, which is present as a loose charge in a storage container, for example a commercially available pharmaceutical vial, tends to agglomerate, by reason of its surface quality and/or its moisture content, resulting in blockage of a comparatively narrow aperture cross section of the vial. Such blockages can normally be obviated only by suitable mechanical means, in order to ensure a continuous dosing of the nebulizable material over quite a long period of time. In addition, agglomerated particles of nebulizable material are not generally able to access the lungs.

In emergency treatment of patients in intensive care in particular, it is necessary to ensure rapid and high-dose administration of pharmaceuticals as nebulizable material, in a form accessible to the alveoli, into the lungs with a constant dosage, in rapid sequence and over a period of several minutes. However, in the prior art, such administration, for example of high-dose pharmaceuticals, was possible, if at all, only with considerable outlay in terms of equipment.

DISCLOSURE OF THE INVENTION

It was therefore an object of the invention to make available a device and a method for dosing and dry nebulization of high-dose pharmaceuticals, in particular anti-infective agents and immunomodulators by means of this device, which overcome the disadvantages known from the prior art.

This object is achieved by the device and methods disclosed herein.

Within the meaning of the present invention, dry nebulization of nebulizable material is understood as its aerosolization, i.e. its conversion into a state carried by carrier gas.

According to the invention, a device is made available in which, in accordance with the principle of a jet pump, a nebulizable material stored in a reservoir is sucked by an underpressure in the reservoir into a nebulization channel and is nebulized in this channel with the compressed gas. The underpressure in the reservoir is in this case generated by the compressed gas flowing past the connection between reservoir and nebulization channel.

The dry nebulizer according to the invention can be used for acute treatment in spontaneously ventilating patients. For this purpose, the second attachment piece of the nebulization channel can be connected via an attachment piece to a device for administration to spontaneously ventilating patients. Examples of such devices are a mouthpiece and breathing mask.

When used on a ventilated patient, i.e. in invasive use, the dry nebulizer is built into the respirator. The second attachment piece of the nebulization channel is in this case preferably joined to the respiratory air intake line of the respirator, in particular to the side port of the respirator.

According to the invention, the duration and/or the time of the pressure pulse from the source of compressed carrier gas is preferably regulated so as to be synchronized, in the case of invasive use, with the respiration rate of the respirator and, in the case of use on spontaneously ventilating patients, with the breathing rate of the patient. According to the invention, a synchronous control is at all times ensured when the mixture of compressed gas and material, that is to say the combination of nebulizable material and compressed carrier gas, reaches the patient before or during an inhalation cycle so that direct uptake of the dry mist by the patient is possible. Of course, the control can also be such that direct uptake of the dry mist by the patient is possible at every x-th breath. The control is such that a control signal is set depending on the length of the nebulization channel and/or of any respirator attachment or attachment piece to a device for administration to spontaneously ventilation patients, and also depending on the desired time of entry of the dry mist into the breathing tube.

Thus, according to the invention, a device is made available in which, during the pressure pulse from the source of compressed carrier gas, i.e. when the valve is opened, an underpressure is present in the reservoir, which underpressure is compensated between the pressure pulses, i.e. when the valve is closed, by gas flowing back. In invasive use of the dry nebulizer according to the invention, the backflowing gas can be a respiratory gas used in the respirator. In the use on spontaneously ventilating patients, it can also be ambient air.

According to the invention, the reservoir is arranged above the nebulization chamber and has a connection to the nebulization channel. This connection is configured so as to be gas-tight with respect to the environment. This connection can consist of one or more openings. By arranging the reservoir above the nebulization channel, the nebulizable material contained in the reservoir collects, as a result of gravity, in the area of the aperture of the reservoir and forms a charge there which, because of the surface quality of the nebulizable material and the choice of a suitable diameter for the aperture(s), prevents the reservoir from emptying into the nebulization channel without output of a pressure pulse. Frictional effects of the particles of the nebulizable material play an important role here. There are no particular restrictions on the connection of the reservoir to the nebulization channel, provided that, when the valve is open to the source of compressed carrier gas, nebulizable material can be sucked into the nebulization channel and the reservoir does not empty into the nebulization channel when the valve is closed.

When the low pressure is applied at the aperture of the reservoir, nebulizable material, on the one hand, but also gas stored in the reservoir, on the other, is sucked into the nebulization channel. As a result, agglomeration of the charge located above the aperture of the reservoir may take place. According to the invention, however, such an agglomeration is broken up by the pressure compensation in the device between the pressure pulses, since ambient air and/or respiratory air flowing back into the nebulization channel also passes through the charge in the reservoir in order to bring about a pressure compensation in the reservoir.

The device according to the invention is designed in such a way that, when the valve is closed, a pressure compensation takes place in the nebulization channel and in the reservoir. This is preferably achieved by the fact that the source of compressed carrier gas is connected to the first attachment of the nebulization channel via a valve in such a way that such pressure compensation is able to take place. According to a preferred embodiment, the pressure compensation is made possible by the fact that the nebulization channel is closed off in a sufficiently gas-tight manner at its first attachment piece. This ensures that the pressure compensation takes place at least for the most part in the nebulization channel and in the reservoir, and not, for instance, via the first attachment piece.

In this way, according to the invention, a uniformly loose charge of the nebulizable material is available after each pressure compensation, as a result of which a step-by-step increasing compaction of the material is avoided and a uniform dosing is guaranteed over a considerable time period. The device according to the invention thus easily allows nebulizable material to be dosed in large amounts in a highly reproducible manner and preferably without mechanical parts. In addition, during the pressure compensation, a loosening of the charge and, if appropriate, a deagglomeration of the nebulizable material is achieved. It is thus possible that the mixture of compressed gas and material predominantly contains particles, preferably exclusively particles, which correspond to the size of the primary particles of the nebulizable material. To this extent, the device according to the invention permits, preferably completely free of mechanical parts, optimal dispersing of the nebulizable material even down to the size of the primary particles.

The size of the primary particles of the nebulizable material preferably corresponds to a mass median aerodynamic diameter (MMAD) which is such that the particles are able to access the lungs, i.e. the site of action in the alveoli of the lungs. The typical MMAD of particles that can access the lungs is in the range of 1 to 10 µm. The desired MMAD range, according to the invention, of the particles in the mixture of compressed gas and material is consequently 1 to 10 µm, preferably 1 to 5 µm, particularly preferably 1-3 µm.

The invention thus provides a device and a method, by means of which a constant dosing of a nebulizable material is ensured over a considerable time period, and with which for example large amounts of pharmaceutical preparations of several grams can also be administered to the patient by inhalation over a comparatively short time period, for example of less than 15 minutes.

The device according to the invention thus doses the amount of material to be nebulized preferably solely on the basis of the amount of compressed gas output per pressure pulse and the duration of this pressure pulse. Further mechanical dosing devices are not required in the device according to the invention.

In an advantageous embodiment of the device according to the invention, a dosing chamber is arranged between the reservoir and the nebulization channel. With a suitable choice of the volume and aperture diameter of this dosing chamber toward the nebulization channel, the dosing of an amount of nebulizable material to be output per pressure pulse can advantageously take place without any restrictions concerning the aperture of the reservoir itself toward the dosing chamber. In a particularly advantageous manner, the diameters of the apertures and of the reservoir and also of the dosing chamber lying below this aperture are matched to one another in such a way that exactly the amount of nebulizable material present within the dosing chamber is nebulized during a pressure pulse.

The source of compressed gas in the device according to the invention can be connected to the nebulization channel via a controllable valve. A controllable valve here is particularly preferably a solenoid valve which, in the manner known to the skilled person, controls the time and duration of a pressure pulse into the nebulization channel. The valve is controlled in a manner adapted to the respiration or ventilation rate of the patient, and, in a preferred embodiment of the device according to the invention, a control signal for the valve is emitted by a pressure sensor which, in invasive use, is located inside the respirator.

According to the invention, a pressure compensation takes place between the pressure pulses in the nebulization channel and the reservoir and, if appropriate, the dosing chamber. This pressure compensation can take place by suitable means in the device through the introduction of ambient air. In an advantageous embodiment of the device, however, this pressure compensation takes place through the introduction of respiratory air or ventilation air counter to the direction of the pressure pulse into the nebulization channel and into the reservoir. In this way, in an advantageous manner, a closed and preferably sterile system can be provided in which contamination by microorganisms or pollutants in the ambient air can be safely avoided.

The compressed gas can advantageously be introduced into the nebulization channel via a capillary which particularly preferably has an internal diameter of 0.8 to 1 mm, very preferably of approximately 1 mm, where the internal or inner diameter is smaller than any inner diameter of the nebulization channel. In a particularly advantageous embodiment of the invention, the outlet of the capillary is arranged in the nebulization channel in the area under the connection between reservoir or dosing chamber and the nebulization channel. In this way, a device is made available in which, in an advantageous manner, a swirling of the compressed gas emerging from the capillary supports the swirling of nebulizable material in the nebulization channel and, consequently, the production of a dry mist. This swirling can additionally contribute to breaking up possible agglomerates of the nebulizable material, so that almost exclusively primary particles of the nebulizable material are present in the obtained mixture of compressed gas and material.

The second attachment piece of the nebulization channel of the device according to the invention is advantageously connected to the respirator attachment piece (in the case of invasive use) or to an attachment piece to a device for administration to spontaneously ventilating patients (in the case of non-invasive use) in such a way that the dry mist, i.e. the mixture of compressed gas and material, is transferred to the patient without said mixture striking against baffle surfaces or other obstacles. In such a configuration of the device, the dry mist can pass unimpeded into the ventilation gas of the respirator and can combine with the ventilation gas there. In this way it is possible to prevent a situation where nebulizable material carried by carrier gas strikes obstacles, settles on these and thus is unable to reach the site of action in the lungs. Particularly with a parallel and very particularly concentric arrangement of nebulization channel and preferably the dispersing nozzle to the respirator attachment or the attachment piece to the device for administration to spontaneously ventilating patients, adherence of nebulized material, for example to the inner walls of the respirator attachment (for example the respirator side port or the breathing tube) or of the mouthpiece, is safely suppressed.

In the device according to the invention, 30 to 180 ml of compressed gas can preferably be introduced into the nebulization channel per pressure pulse. In this way it is possible to make available an amount of compressed gas that is particularly advantageous for the nebulization of the desired amount of nebulizable material, and which amount is sufficient to nebulize an amount of nebulizable material which can be taken up by the lungs of the patient in question. At the same time, the amount to be nebulized with such a volume of compressed carrier gas is sufficiently small to exclude the possibility of the patient's breathing or ventilation being adversely affected.

In a further advantageous embodiment of the device according to the invention, a predefined amount of the powdered material, preferably 10 to 50 mg, particularly preferably 10 to 30 mg, can be nebulized per pressure pulse. Thus, a device is made available which in a particularly simple manner permits a uniformly dosed nebulization of powdered material in an amount which is advantageously adapted to the uptake capacity of the lungs of the patient.

The reservoir for the nebulizable material is connected to the device and is preferably a conventional vial for injectable preparations. Its external diameter is typically in the range of 2 cm. Before the vial is fitted on the device according to the invention, its closure piece, usually a rubber stopper, is removed.

In a further preferred embodiment of the device according to the invention, the reservoir contains 0.1 to 3 g, more preferably 0.5-3 g, particularly preferably 1 to 2 g, of nebulizable material. This means that, in a particularly advantageous manner, the amount of material to be nebulized by the device can be adapted to the dose and duration of administration required particularly in intensive care medicine in inhaled administration of powdered pharmaceutical preparations.

Within the meaning of the application, nebulizable material is understood as a material from which at least some converts into a state carried by carrier gas during operation of the device according to the invention.

According to the invention, the nebulizable material is a high-dose pharmaceutical preparation which can be administered in particular by inhalation. This pharmaceutical preparation is advantageously powdered, for example a micronized powder. The production of powdered pharmaceutical preparations of this kind, for example by means of micronization processes, will be familiar to the skilled person. The nebulizable material can, for example, be a pharmaceutical preparation, except for a lung surfactant. The nebulizable material is preferably chosen from the group comprising anti-infective agents and immunomodulators. Within the meaning of the application, the term "anti-infective agents" is to be understood as including all substances which inhibit or kill infectious agents. Examples of anti-infective agents are antibiotics, antivirals, antimycotics and antiprotozoal agents. Here, "antibiotics" are understood as substances with bacteriostatic or bactericidal action. Within the meaning of the application, "immunomodulators" are substances which have a modulating effect on the immune system, for example immunosuppressives. Of course, the nebulizable material can also include mixtures of such substances.

Examples of antibiotics that can be used are penicillins, cephalosporins, carbapenems, monobactams, tetracyclines, aminoglycosides and gyrase inhibitors, or any desired combinations thereof. Examples of penicillins that can be used are amoxillin, ampicillin, azidocillin, benzylpenicillin, flucloxacillin, phenoxymethylpenicillin and piperacillin. Examples of cephalosporins that can be used are cefaclor, cefepime, cefixime, cefotaxime, cefotiam, cefpodiximproxetil, ceftazidime, ceftibuten, cetriaxone, cefuroxime, cefuroximaxetil, cefadroxil, cefalexine, cefazolin and loracarbef. Examples of carbapenems are ertapenem and meropenem. An example of a monobactam that can be used is aztreonam. Examples of tetracyclines that can be used are doxycycline and minocycline. Examples of aminoglycosides that can be used as nebulizable material according to the invention are amikacin, tobramycin, netilmicin, gentamicin and streptomycin. Suitable gyrase inhibitors are, for example, moxifloxacin, ciprofloxacin and ofloxacin. Other examples of antibiotics are fosfomycin, telithromycin and linezolid.

Examples of immunomodulators are cyclosporin and azathioprine.

Examples of antiprotozoals that can be used as anti-infective agent are pentamidine and atovaquone.

In all cases, any desired mixtures of these and other substances can be used as nebulizable material as long as at least some of this mixture can be converted into a state carried by carrier gas during operation of the device according to the invention.

According to a further aspect of the invention, a method is made available for dosing and dry nebulization of nebulizable material by means of an above-described device. This method includes the steps of introducing a pressure pulse into the nebulization channel, in order to generate an underpressure in the reservoir for the nebulizable material, the resulting sucking of a subsidiary amount of the nebulizable material into the nebulization channel, and the aerosolization of this subsidiary amount inside the nebulization channel. After the mixture of compressed gas and nebulizable material has passed through the dispersing nozzle into the breathing tube or the like, pressure compensation takes place after completion of each pressure pulse in which introduced air from the outside and/or respiratory air flows back from the breathing tube or the like into the nebulization channel and the reservoir.

According to the invention, during this pressure compensation, the gas flows through the charge of material which is located above the aperture of the reservoir and if appropriate above the aperture of the dosing chamber, and which is possibly compacted and agglomerated there, and the latter is thus loosened and deagglomerated.

If, during the preceding pressure pulse, a dosing chamber that may have been used is completely emptied, a charge of material agglomerated above the aperture of the reservoir falls into the dosing chamber and forms a charge above the aperture of the dosing chamber to the nebulization channel. Thus, by particularly simple means, a targeted dosing of the pharmaceutical preparation inside the device is achieved.

In a further preferred embodiment of the method according to the invention, by repeating the steps described above, the content of the reservoir is completely nebulized and delivered to the patient within a defined time period of preferably less than 15 minutes, particularly preferably of less than 10 minutes. In this way, a method is made available which particularly advantageously satisfies the requirements in intensive care of patients or in emergency treatment of patients, where rapid administration of high doses of pharmaceutical preparations is necessary.

BRIEF DESCRIPTION OF THE DRAWINGS

The invention is explained in more detail below by way of example and with reference to FIGS. 1 to 5. The devices shown in the figures simply represent advantageous embodiments of the invention and are not intended to in any way limit the underlying concept of the invention.

In the figures.

EMBODIMENTS OF THE INVENTION

Figure 1:
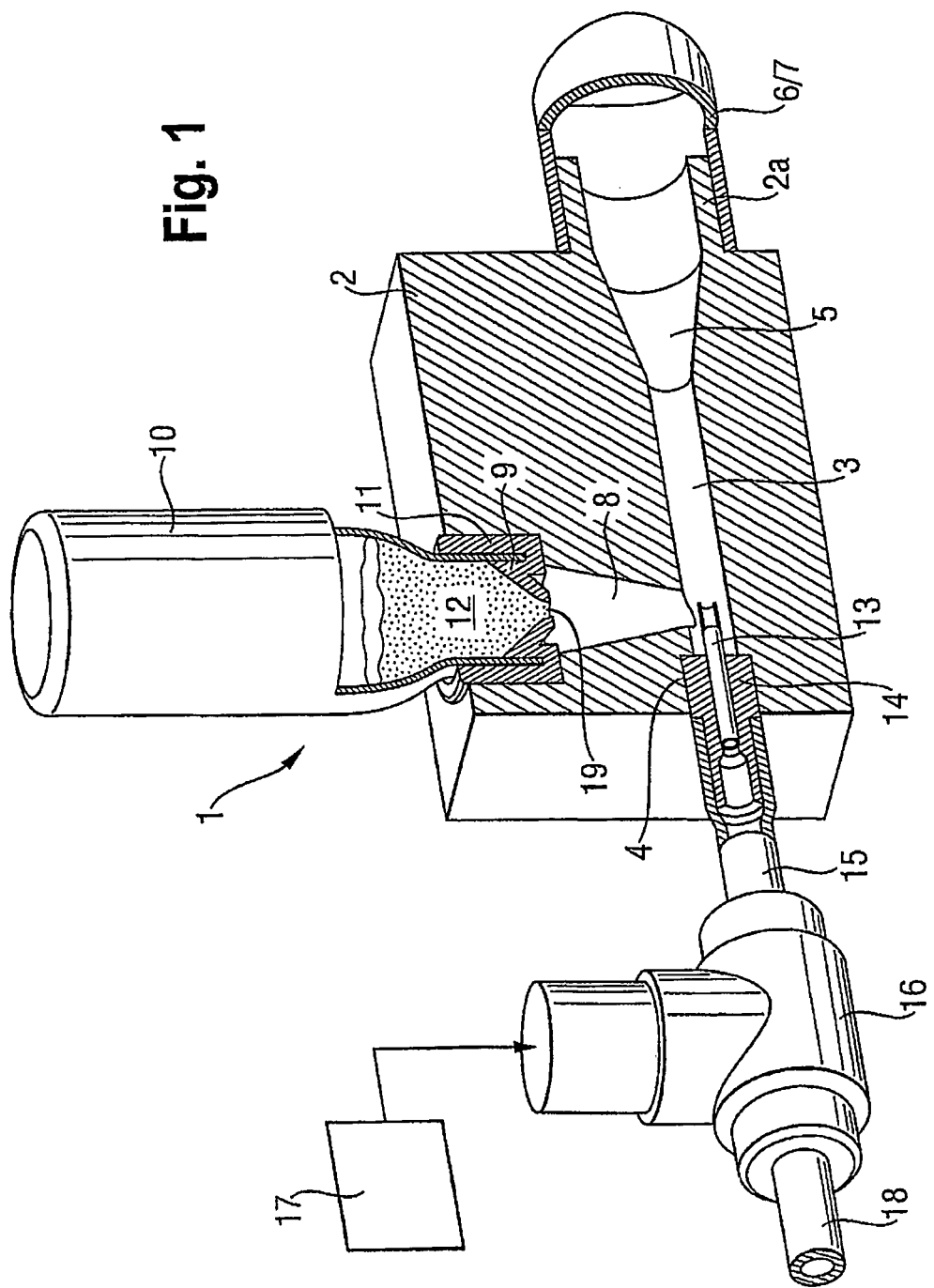
FIG. 1 shows a schematic representation of a first embodiment of the device according to the invention.

In FIG. 1, a partially sectioned, perspective view of the device 1 is shown in which a nebulization channel 3 is arranged inside a nozzle block 2. At its first end (on the left in FIG. 1), the nozzle block 2 comprises a capillary seat 4 into which a capillary tube holder 14 supporting a capillary tube 13 is fitted. This capillary tube holder 14 is in turn connected to a connecting line 15 which opens into a solenoid valve 16, the latter being regulated by a control system labelled schematically with reference number 17. The flow of the compressed gas from the compressed air attachment line 18 into the capillary tube 13 is regulated by the control system 17. At its second end (on the right in FIG. 1), the nebulization channel 3 opens into a dispersing nozzle 5 whose cross section increases continuously in a direction extending away from the capillary tube 13. The dispersing nozzle 5 in turn opens into an attachment piece 2a which is an integral component part of the nozzle block 2 onto which is fitted a respirator attachment piece 6 or an attachment piece 7 to a device for administration to spontaneously ventilating patients. The device 1 also comprises, above the nebulization channel, a receiving seat 9 for the medicament reservoir 10. The upper edge 11 of the reservoir 10 is fitted into the receiving seat 9 provided in the nozzle block 2, the aperture 19 of the reservoir 10 being located above a dosing chamber 8 with a conically tapering shape. Located above this aperture 19 is a charge of the pharmaceutical preparation 12 which is agglomerated to such an extent that almost no grain of the nebulizable material 12 enters the dosing chamber 8.

Figure 2:
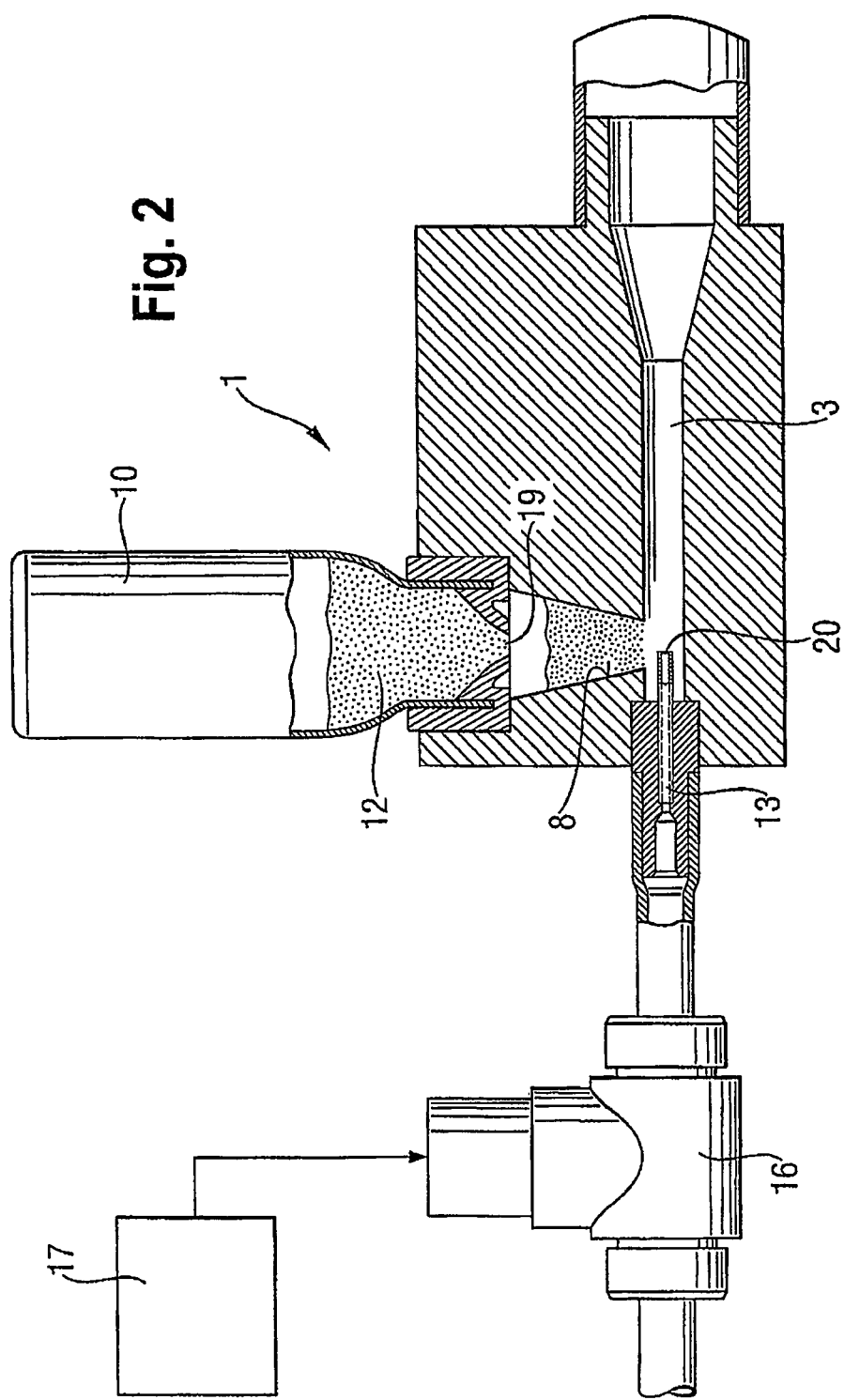
FIG. 2 shows a partially sectioned side view of a first embodiment of the device according to the invention.

FIG. 2 shows a partially sectioned side view of the device 1 shown in FIG. 1, but, in contrast to the view shown in FIG. 1, with the dosing chamber 8 already filled. In this state of the device 1, the dosing chamber 8 has been filled by material falling through the aperture 19 until the material 12 in the reservoir 10 has compacted to the extent that no further material 12 can slip into the dosing chamber 8. At the time shown in FIG. 2, the control system 17 has not emitted any signal to the solenoid valve 16, so that no compressed air passes through the valve 16 and the capillary tube 13 into the nebulization chamber 3.

Figure 3:
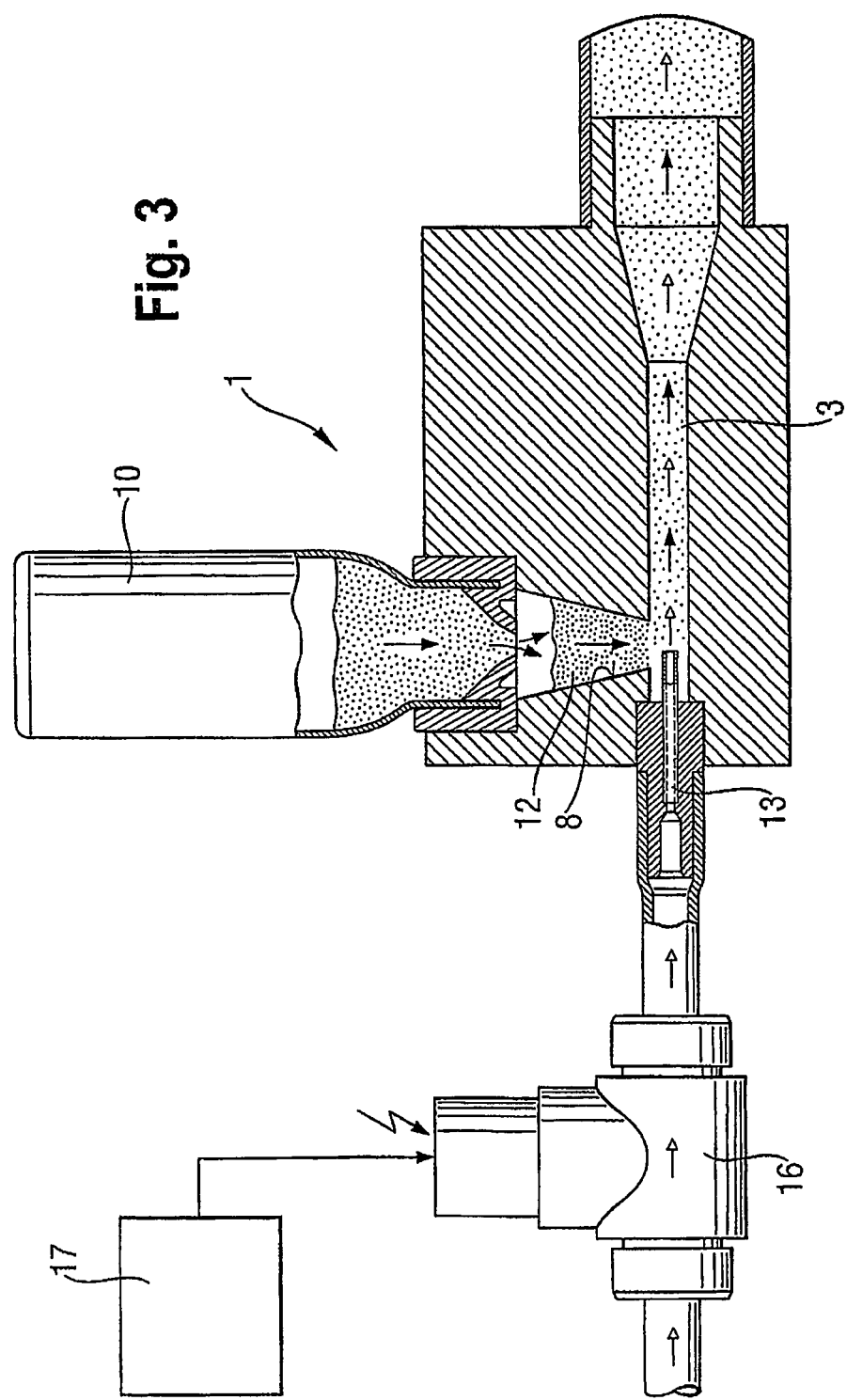
FIG. 3 shows the state of a device according to the invention during output of a pressure pulse into the nebulization chamber.

FIG. 3 shows a partially sectioned side view of the device 1 at a time after the control system 17 has sent an opening signal to the solenoid valve 16. From this time onwards, compressed air passes through the solenoid valve 16 and the capillary tube 13 into the nebulization channel 3. In the nebulization channel 3, an underpressure is created by the flow of the compressed air in the reservoir 10 and in the dosing chamber 8, by means of which underpressure at least the charge of material 12 present in the dosing chamber 8 is entrained in the stream of compressed air, which is indicated by the empty arrows. In the nebulization channel 3, the nebulizable material 12 is aerosolized with the compressed air, such that the dry mist, indicated by the presence of filled arrows and also empty arrows, is guided into the respirator attachment 6 and the attachment piece 7. The dry mist generated in this way can be transported with the respiratory air or ventilation gas into the lungs of the patient.

Figure 4:
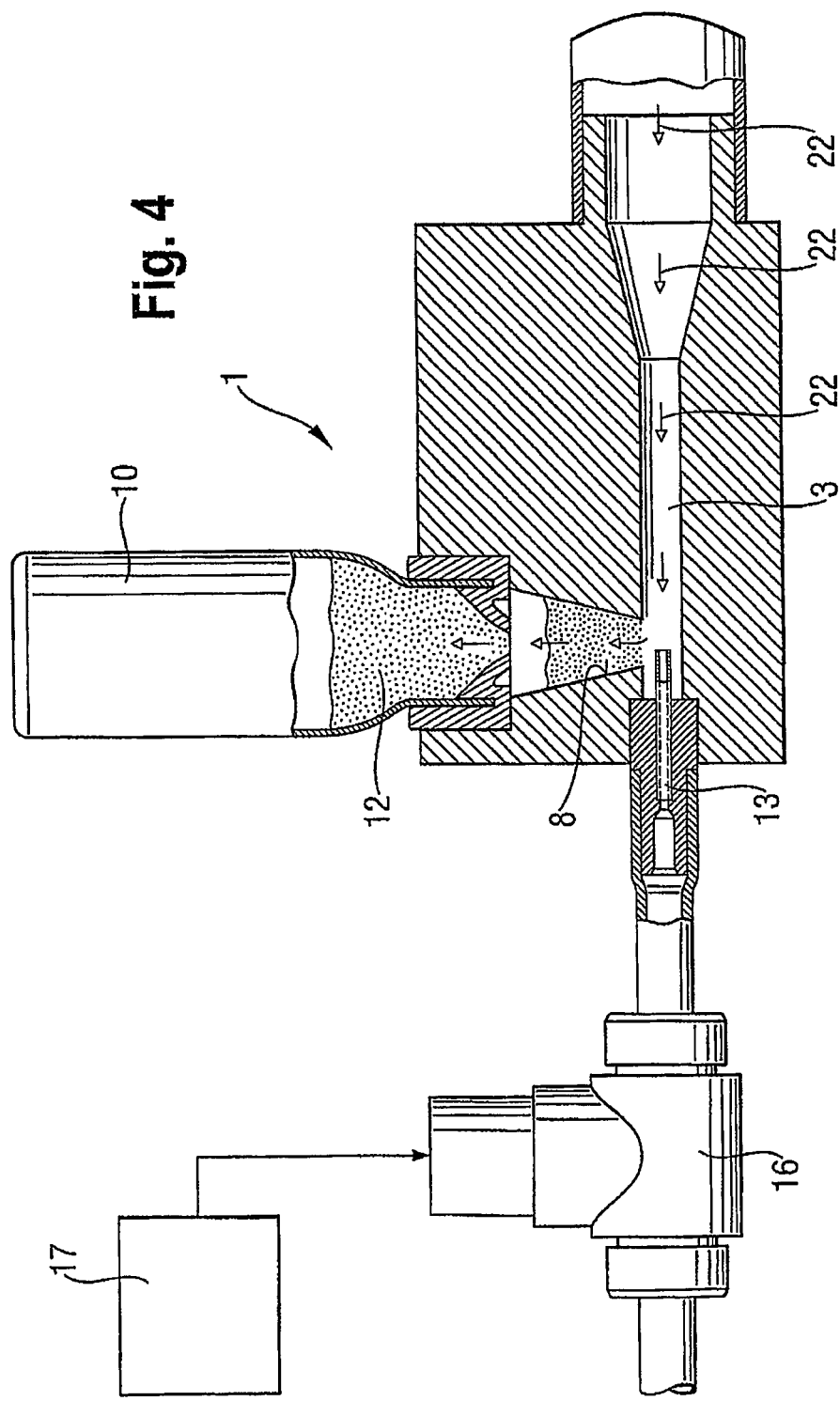
FIG. 4 shows a state of the device according to the invention during a time period between two pressure pulses.

FIG. 4 shows a partially sectioned side view of the first embodiment of the device 1 according to the invention at a time when the control system 17 sends no opening signal to the solenoid valve 16, as a result of which the steam of compressed gas from the compressed-gas source (not shown) into the nebulization channel 3 is also interrupted. On account of the pressure gradient, for example between the respiratory air intake line of the respirator or of the device for administration to spontaneously ventilating patients and of the device 1, ventilation air or respiratory air flows into the nebulization channel 3 and through the dosing chamber 8 into the reservoir 10. By means of the air stream (indicated by the arrows 22) through the respective charges of material in the dosing chamber 8 and the reservoir 10, the charges are loosened and any agglomerations are broken up, so that, after pressure compensation has taken place, nebulizable material 12 that is able to flow is present in the device 1.

Figure 5:
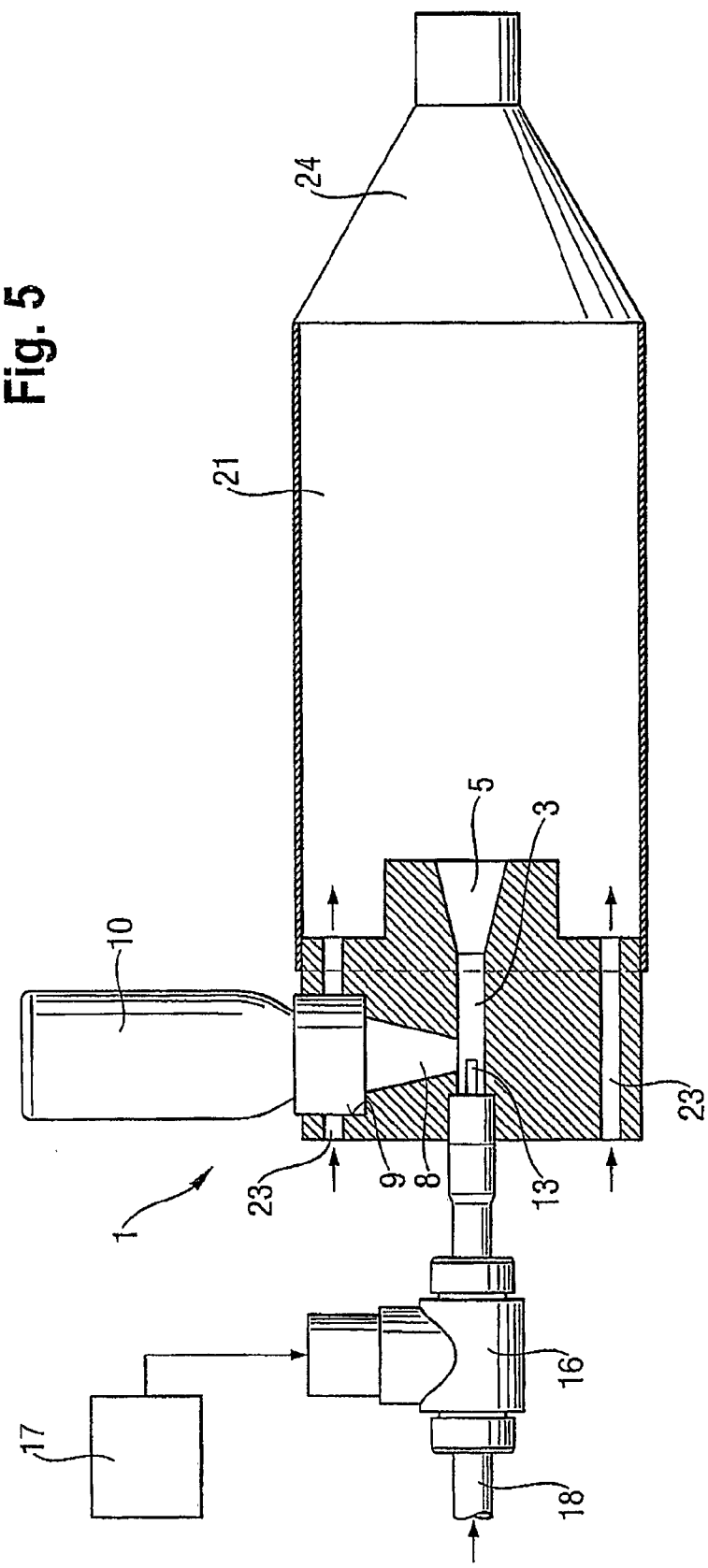
FIG. 5 shows a partially sectioned schematic side view of a second embodiment of the device according to the invention.

FIG. 5 shows an embodiment of the device 1 according to the invention in which the device 1 is arranged concentrically with respect to a cylindrical breathing tube 21. In this embodiment too, compressed gas flows through the compressed air attachment line 18 and the capillary tube 13 into the nebulization channel 3 after the solenoid valve 16 is opened, which solenoid valve 16 is regulated by a control system 17. In this case too, directly above the open end of the capillary tube 13 is the aperture of the dosing chamber 8, above which the reservoir 10 is positioned in a receiving seat 9 provided for it. In this embodiment, the longitudinal axis of the nebulization channel 3 lies on the longitudinal axis of the breathing tube 21 and parallel to a multiplicity of respiratory air intake openings 23 through which respiratory air is conveyed from a source (not shown) through the breathing tube 21. Finally, at its end remote from the device 1, the breathing tube 21 ends in a schematically depicted mouthpiece 24 around which the patient can place his or her lips, so as to inhale the respiratory air to which the dry mist has been added.

The invention claimed is:

1. A method for dosing and dry nebulization of nebulizable material, comprising the steps of:
    providing a nebulization channel, the nebulization channel being configured to allow attachment to a respirator or to a device for administration of the nebulizable material to spontaneously ventilating patients;
    providing a reservoir containing the nebulizable material above and open only towards the nebulization channel, with the nebulizable material having primary particles with a mass mean aerodynamic diameter (MMAD) of 1 to 10 micrometers ($\mu$m), the reservoir connected to the nebulization channel in a gas-tight manner with respect to an environment;
    providing a dosing chamber arranged between the reservoir and the nebulization chamber, the dosing chamber having a tapered conical shape; wherein a predefined amount of nebulizable material from the reservoir flows into the dosing chamber;
    providing a capillary tube having an inner diameter smaller than any inner diameter of the nebulization channel, the capillary tube having an outlet in an area under the dosing chamber;
    releasing a carrier gas pressure pulse by a controllable valve into the capillary tube, the valve being controlled by a control signal, such that upon the carrier gas pressure pulse exiting the capillary tube into the nebulization channel, the capillary tube and the nebulization channel form a jet pump generating an underpressure in the dosing chamber by the carrier gas pressure pulse flowing past the dosing chamber, thereby sucking the nebulizable material present in the dosing chamber into the nebulization channel and nebulizing the nebulizable material in the channel with the carrier gas pressure pulse; wherein exactly the predefined amount of nebulizable material is nebulized during the carrier gas pressure pulse; and
    closing the valve to create a pressure compensation by respiratory gas or ventilation gas flowing back through the dosing chamber and into the reservoir, wherein the pressure compensation loosens nebulizable material remaining in the reservoir.

2. The method according to claim 1, further comprising the step of delivering multiple pulses and, between pulses, allowing the respiratory gas or ventilation gas to flow into the nebulization channel and into the reservoir counter to a direction of the pressure pulse.

3. The method according to claim 1, further comprising the steps of:
    connecting an attachment piece to the nebulization channel; and
    connecting a respirator to the attachment piece.

4. The method according to claim 3, further comprising the step of concentrically connecting the nebulization channel to the attachment piece.

5. The method according to claim 1, further comprising the step of synchronizing a duration and/or time of the carrier gas pressure pulse with a respiratory rate of a respirator.

6. The method according to claim 1, wherein the nebulized material is administered to spontaneously ventilating patients.

7. The method according to claim 6, further comprising the step of synchronizing a duration and/or time of the pressure pulse with a respiratory rate of a patient who is spontaneously ventilating.

8. The method according to claim 1, further comprising the step of introducing 30-180 ml of carrier gas into the nebulization channel per pressure pulse.

9. The method according to claim 1, wherein the reservoir contains 0.1 to 3 g of nebulizable material.

10. The method according to claim 1, wherein the nebulizable material is powdered.

11. The method according to claim 1, wherein the nebulizable material is an anti-infective agent selected from the group consisting of antibiotics, antivirals, antimycotics, and antiprotozoal agents.

12. The method according to claim 11, wherein the anti-infective agent is an antibiotic chosen from the group of penicillins, cephalosporins, carbapenems, monobactams, tetracyclines, aminoglycosides, gyrase inhibitors, and mixtures thereof.

13. The method according to claim 1, further comprising the step of loosening the nebulizable material using the respiratory gas or ventilation gas flowing through the nebulizable material.

14. The method according to claim 1, wherein the nebulizable material within the reservoir is almost completely nebulized within a defined time period.

15. The method according to claim 1, wherein a source of compressed carrier gas is connected to the capillary tube via the controllable valve, and the connection of the source of compressed carrier gas to the capillary tube, via the valve, is sufficiently gas-tight.

* * * * *